United States Patent [19]

Rechsteiner et al.

[11] Patent Number: 5,366,871
[45] Date of Patent: Nov. 22, 1994

[54] UBIQUITIN-PEPTIDE EXTENSIONS AS ENZYME SUBSTRATES

[75] Inventors: Martin C. Rechsteiner; Yung J. Yoo, both of Salt Lake City, Utah

[73] Assignee: The University of Utah, Salt Lake City, Utah

[21] Appl. No.: 791,935

[22] Filed: Nov. 13, 1991

[51] Int. Cl.$^5$ .................. C12Q 1/37; C12Q 1/48; C12P 19/04

[52] U.S. Cl. ................... 435/24; 435/15; 435/101; 435/105; 435/193; 530/335

[58] Field of Search ............... 435/101, 105, 15, 24, 435/193, 814, 815; 530/335, 413

[56] References Cited

U.S. PATENT DOCUMENTS

| | | | |
|---|---|---|---|
| 5,043,268 | 8/1991 | Stock | 435/15 |
| 5,141,851 | 8/1992 | Brown | 435/15 |
| 5,185,248 | 2/1993 | Barbacid | 435/15 |

OTHER PUBLICATIONS

Yoo, Y., Synthesis of Peptides as Cloned Ubiquitin Extensions, J. of Biol Chemistry, vol. 264 #29 1989, pp. 17078-10783.

Marin, O., Synthetic Peptides Including Acidic Clusters . . . Int J. Protein Res 36 #4, 1990, pp. 374-380.

Yoo, Y., Ubiquitin-Ras Peptide Extensions as Substrates . . . Biochem Journal vol. 285 Part 1 1992 pp. 55-60.

*Primary Examiner*—Michael G. Wityshyn
*Assistant Examiner*—Ralph Gitomer
*Attorney, Agent, or Firm*—Thorpe, North & Western

[57] ABSTRACT

A method for assaying for enzymes that modify peptide chains, such as protein kinases and enzymes which modify the C-terminus of the Ha-RAS protein, is defined. This is done by incubating an extract in which the enzyme being assayed for may be present contained in a reaction mixture. The reaction mixture is made up of a buffer solution, a ubiquitin peptide extension, wherein the peptide contains a sequence known to be modified by an agent in the presence of the enzyme being assayed for, and the agent known to modify the peptide extension when the enzyme is present. The incubation is stopped and the ubiquitin peptide extension is separated from the solution and analyzed for the presence of the agent modified peptide. The extent of peptide modification can be both qualitative and quantative of the enzyme being assayed for. Protein kinases can be assayed for using a ubiquitin pepide extension containing the sequence (SEQ ID NO:1), Ser-Glu-Glu-Glu-Glu-Glu in the presence of a phosphorylating agent. Farnesyl-protein transferase can be assayed for using a ubiquitin-peptide extension with the sequence: Pro-Gly-Cys-Met-Ser-Cys-Lys-Cys-Val-Leu-Ser, (SEQ ID NO:11) which are the eleven C-terminal residues of the RAS molecule, in the presence of a farnesylating agent such as $^3$H-farnesyl pyrophosphate. Carboxyl methyl transferase can be assayed for using a farnesylated ubiquitin-peptide extension in the presence of a methylating agent such as tritium labeled as [$^3$H-methyl]AdeMet.

32 Claims, 1 Drawing Sheet

Figure 1

UBIQUITIN-PEPTIDE EXTENSIONS AS ENZYME SUBSTRATES

This invention was made with government support under Grant Number GM 37009 awarded by the National Institutes of Health and Grant Number CDV395-02 from the American Cancer Society. The government has certain rights in this invention.

BACKGROUND OF THE INVENTION

This invention relates to Ubiquitin peptide extensions which serve as substrates for assaying for enzymes that modify peptide chains. More particularly, this invention relates to cloned Ub-peptide extensions as novel substrates for assaying protein kinases or enzymes that modify the C-terminus of the Ha-RAS protein.

Among the enzymes left to be discovered and characterized, many catalyze reactions in which proteins are the substrate. These classes of enzymes include the ever-expanding families of protein kinases (see Edelman et al., *Ann. Rev. Biochem* (1987) 56:567-613 and Hunter, *Curr. Opinion Cell Biol.* (1989) 1:1168-1181). The central importance of protein kinases in controlling cell behavior becomes so evident with each passing year that this point now needs little emphasis (see Hunter et al., *Annu. Rev. Biochem.* (1985), 54:897-930; Edelman et al., supra; Taylor, *Bioessays*(1987), 7:24-29; and Kikkawa et al., *Annu. Rev. Biochem.*, (1989), 58:31-44 for review). What remains surprising, however, is the large number of different kinases present in eucaryotic cells.

Kuenzol et al., *J. Biol. Chem.*, (1987), 262:9136-9140; Meggio et al., *FEBS Lett.*, (1988), 237:225-228; Abdel-Ghany et al., *Proc. Nat. Acad. Sci. USA,* (1988), 85:1408-1411; Yasuda et al., *Biochem. Biophys. Res. Commun.*, (1990), 166:1220-1227 and Litchfield et al., *FEBS Lett.*, (1990), 261:117-120 all have shown that synthetic peptides can be used both to assay protein kinases and to deduce the amino acid sequences required for phosphorylation by the enzymes. Deana et al., *Biochim. Biophys. Acta,* (1990), 1051:199-202 demonstrates that synthetic peptides also permit assay of protein phosphatases.

Other enzymes that catalyze reactions in which proteins are the substrate include enzymes that add lipids to proteins (see Glomset, et al., *TIBS* (1990), 15:139-142 and Gordon, et al., *J. of Biol. Chem.* (1991), 266:8647-8650) and a wide variety of enzymes that modify specific amino acid side chains on cellular and secreted proteins (see Clark, *Ann. Rev. Biochem.* (1985), 54:479-506, Hart et al., *Ann. Rev. Biochem.* (1989),58:841-874 and Rechsteiner, *Ubiquitin* (1989) Plenum Press, 346 pp.

Examining the substrate specificity of that many enzymes is a formidable task. Analysis of such enzymes requires peptides, either as potential substrates for measuring kinetic features of these catalysts or in the preparation of affinity matrices for purifying them. Means for identifying and assaying enzymes per se is a commercial venture in which many business entities are engaged. Enzymes are used in detergents, in diagnostic testing, as keys to biotech operations. It is likely that enzymes will be used on an industrial scale in future applications.

In this regard, small peptides obtained as Ub extensions offer distinct advantages over smaller peptide substrates. First, they are less expensive to synthesize in large quantities. Also, Ub-peptides can, in certain cases, be purified from bacterial extracts by simple acid extraction. Some enzyme assays may require electrophoretic analysis for accurate quantitation and the fact that Ub-peptides migrate on SDS-PAGE gels in a region ($\sim$9K) virtually devoid of other proteins that may also become modified is a distinct advantage of the use of Ub-peptide extensions over the peptide alone. Furthermore, the presence of Ub at the N-terminus of the peptide substrate is thought to be crucial for product capture by PDVF or other electroblotting membranes. Another important advantage of ubiquitin-peptide extensions is the availability of proteases able to remove precisely the peptide extension from ubiquitin without further cleaving the released peptide.

The present invention therefore depends to a large extent on ubiquitin, a remarkable small protein with a variety of useful properties. Ubiquitin is a highly conserved, 76-residue protein having a C-terminus composed of arg-gly-gly and is found in all eucaryotic cells both free and covalently conjugated to a variety of cellular proteins. Ubiquitin is found in cells as diverse as mammals, yeast and celery. Ubiquitin is attached by its carboxyl terminus to amino groups of other proteins. When ubiquitin is attached to the alpha-amino terminus, such products are referred to in the literature as ubiquitin carboxyl extension proteins. In eucaryotic cells, the extension proteins are cleaved from the ubiquitin molecule by hydrolases (peptidases). It has been postulated that attachment of ubiquitin to a protein is a signal for the latter's destruction by proteolysis. Ubiquitin is lacking in cysteine and tryptophan but there is nothing unusual about its sequence other than its extreme conservation. The identical sequences of animal ubiquitins differ only at three positions from the yeast and plant ubiquitin. The x-ray structure of ubiquitin, which has been resolved to 2.8 A, reveals a compact globular protein with the carboxyl terminal arg-gly-gly extended into the solvent. The molecule contains four strands of (beta)-sheet plus a single (alpha)-helix with three and one half turns; all sequence differences among species being located on a small portion of the ubiquitin surface. NMR studies have shown that ubiquitin remains folded at pHs of 1 to 13 and below 80° C. A distinct hydrophobic core and extensive hydrogen bonding are present, which may account for the molecule's exceptional stability. Ubiquitin has a neutral isoelectric point of 6.7 and a molecular weight of 8565. Ubiquitin is not only stable to extremes of pH, as noted above, but also to heat.

For a detailed analysis of ubiquitin, its properties and functions, reference is made to the book "Ubiquitin", published by Plenum Press, N.Y. (1989) and edited by Martin Rechsteiner.

Ubiquitin is an extremely soluble protein that can be expressed to very high levels within *E. coli* cells as shown by Butt et al., *Proc. Nat. Acad. Sci. USA,* (1989), 86:2540-2544. Carboxyl terminal peptide extensions are easily and cheaply prepared by cloning in *E. coli*. For example, the preparation of synthetic ubiquitin peptide fusion products containing up to about forty additional amino acid residues as ubiquitin extensions expressed in procaryotic cells, such as in *E. coli*, is described by Rechsteiner et al., copending patent application Serial No. 07/420,544 filed Oct. 12, 1989 and by Yoo et al., *J. Biol. Chem.* (1989) 264:17078-17083. Another important advantage of ubiquitin-peptide extensions is the availability of ubiquitin hydrolase enzymes able to remove precisely the peptide extension without further cleaving the released peptide.

Because some of the Ub-peptide extensions described herein contain a modified ubiquitin, a 76-residue protein, in which the last three amino acids of the C-terminus, composed of arg-gly-gly in native ubiquitin, have been changed to prevent cleavage by the ubiquitin hydrolase enzymes, the term $Ub_{73}$ is sometimes used to designate the N-terminal 73 residues of ubiquitin. When the term "Ub-" followed by a specific designation is used, the ubiquitin referred to can be either the native 76 residue molecule or a molecule in which the last three residues of arg-gly-gly have been modified, as in the Ub-AEX designation. However, it will be clear from the specific designation used whether the ubiquitin is native or modified at the last three residues.

The ubiquitin molecule has several characteristics that make it particularly valuable as a carrier of peptides containing specific enzyme assaying characteristics. Native ubiquitin itself does not appear to be a suitable substrate for enzyme assays.

Therefore, while short chain peptides are commercially available for use as substrates in assaying for enzymes, they are expensive, difficult to synthesize and are not particularly useful in some assay techniques, such as being immobilized on membranes.

Assaying for enzymes, both qualitatively and quantitatively, can provide a useful diagnostic tool for examining antibodies or enzymes which, when present, may be indicative of certain diseases or other medical conditions.

The HaRAS protein, for example, has a molecular weight of about 21 KDa and is made up of 189 amino acid residues. It is an oncogene protein product which is mutant in about fifty percent of human tumors and attached to the cell surface at its C-terminus. It is known that lipid transfer enzymes, such as farnesyl-protein transferase (FPT), and methyl transfer enzymes, such as carboxyl methyltransferase, both modify RAS by reactions at the C-terminal end of the RAS molecule as will be shown below. Therefore, it is likely that a suitable clinical assay for the presence of enzymes that modify the C-terminus of RAS, either in normal or abnormal levels, can be a diagnostic tool in the science of oncology.

Protein kinases are also known to be mutated in human tumors and are active by adding phosphates on protein residues on the surface of cells.

It would therefore be highly beneficial in the art of enzymology to provide a substrate containing any multiplicity of peptide sequences which can readily and economically be cloned and utilized in a variety of assay techniques and/or diagnostic tests for enzymes which will react with such substrate.

OBJECTS AND BRIEF SUMMARY OF THE INVENTION

It is an object of the present invention to prepare synthetic ubiquitin peptide extensions wherein the peptide extension is a suitable substrate for use in assaying for enzymes.

Also an object of this invention is to provide a technique for the assay of enzymes which are reactive to or modify peptides at the plasma membrane.

Another object of this invention is to provide cloned Ub-peptide extensions which are useful as protein kinase substrates.

An additional object of this invention is to provide Ub-peptide extensions which are particularly useful as substrates for assaying for casein kinase II activity.

It is also an object of this invention to synthesize cloned Ub-cRAS extensions as substrates for assaying certain that modify the C-terminus of the Ha-RAS protein.

A still further object of the invention is to provide a Ub-cRAS extension protein as a suitable substrate for modification by farnesyl-protein transferase and carboxyl methyl transferase.

Another object of the invention is to provide an easy membrane-binding assay for detecting enzyme activity using Ub-peptide substrate.

These and other objects may be accomplished by means of preparing appropriate oligonucleotides encoding the desired peptide as a ubiquitin peptide extension gene, splicing the gene into an appropriate plasmid which, in turn is transformed into *E. coli*, or other appropriate procaryotic cells capable of expressing the ubiquitin extension peptide. When expressed, the cells produce recoverable amounts of ubiquitin extended at its carboxyl terminus by the encoded peptide.

In specific and preferred embodiments the ubiquitin molecule is extended by a peptide containing the amino acid sequence Ser-Glu-Glu-Glu-Glu-Glu (SEQ ID NO:1) which serve as protein kinase substrates and have the formulas:

$Ub_{73}$—Arg—Gly—Gly—Met—Glu—Phe—Met—His—Ile—Ser—Pro—Pro—Glu—Pro—Glu—Ser—Glu—Glu—Glu—

Ub-PEST4 (SEQ ID NO:3)
$Ub_{73}$-Arg-Gly-Gly-Met-Glu-Phe-Met-His-Glu-Ser-Glu-Glu-Glu-Glu-Glu-His-Ser-Ser
Ub-AEX (SEQ ID NO:4)
$Ub_{73}$-Gln-Gly-Ala-Met-Glu-Ala-Ser-Glu-Glu-Glu-Glu-Glu-Phe and also a peptide consisting of eleven amino acids from the C-terminus of Ha-RAS to provide a Ub-cRAS molecule which serves as a substrate for assaying certain enzymes that modify the C-terminus of the Ha-RAS protein and has the formula:
Ub-cRAS(Cys-Val-Leu-Ser) (SEQ ID NO:5)
$Ub_{73}$-Arg-Gly-Gly-Pro-Gly-Cys-Met-Ser-Cys-Lys-Cys-Val-Leu-Ser
where $Ub_{73}$ stands for the N-terminal 73 amino acids from ubiquitin and (Cys-Val-Leu-Ser) is the one letter amino acid code for the terminal four amino acids Cys-Val-Leu-Ser in the peptide extension.

The process is adaptable to the production of any desirable peptide extensions, in addition to those mentioned above, which are suitable for assaying targeted enzymes.

The Ub-PEST1 (SEQ ID NO:2), Ub-PEST4 (SEQ ID NO:3) and Ub-AEX (SEQ ID NO:4) extensions are all suitable substrates for the assay of protein kinases. Casein kinase II (CKII) is known to phosphorylate serines or threonines bordered on their C-terminus by several glutamate residues according to Meggio, et al, supra. The Ub-PEST1 and Ub-PEST4 molecules were therefor selected as suitable substrates for assaying CKII activity. When subjected to an extract of partially purified rabbit reticulocyte CKII and processed by electrophoretic analysis followed by autoradiography it was demonstrated that casein and the Ub-PEST1 and UB-PEST4 extensions were readily phosphorylated. By contrast, other Ub-peptide extensions having the following formulas:

Ub-PEST2 (SEQ ID NO:6)
Ub$_{73}$-Arg-Gly-Gly-Met-Glu-Phe-Met-His-Glu-Ser-His-Ser-Ser

Ub-PEST3 (SEQ ID NO:7)
Ub$_{73}$-Arg-Gly-Gly-Met-Glu-Phe-Met-His-Ile-Ser-Pro-Pro-Glu-Pro-Glu-Ser-His-Ser-Ser were not substrates for CKII even though together they contain as many serine residues as the Ub-PEST1 and Ub-PEST4 products. Ubiquitin per se was found to be refractory to phosphorylation.

The Ub-extensions which are phosphorylated by CKII provide analytical flexibility in that they were found to offer at least three methods for measuring protein kinase activity, i.e. binding to ion-exchange paper, acid precipitation, or SDS-PAGE followed by autoradiography.

Because of the potential that specific proteases present in crude extracts being assayed for CKII activity might cleave the peptide extensions from ubiquitin, the last three residues, i.e. the 74-76 residues, Arg-Gly-Gly of ubiquitin were changed to Gln-Gly-Ala in constructing the Ub-AEX (SEQ ID NO:4) extension protein which was followed by the residues Met-Glu-Ala-Ser-Glu-Glu-Glu-Glu-Glu-Phe (SEQ ID NO:8).

Altering the last three residues of ubiquitin did not greatly reduce the yield of peptide extension upon induction of E. coli but did product an extension protein that could not be cleaved by the cell's normal ubiquitin carboxyl-terminal hydrolase. When the three proteins, Ub-PEST1 (SEQ ID NO:2), Ub-PEST4 (SEQ ID NO:3) and Ub-AEX (SEQ ID NO:4), were added to crude extracts containing [$\gamma$-$^{32}$P]ATP and, after incubation, the reaction mixtures were analyzed on SDS-PAGE followed by autoradiography, all showed phosphorylation. However, the cleavable Ub-PEST1 and Ub-PEST4 incorporated more $^{32}$PO$_4$ than the Ub-AEX.

The above Ub-peptide extension as particularly effective as substrates for reticulocyte CKII enzymes. These Ub-peptide extension also offer unique opportunities for locating phosphorylated residues in sequences containing several potential kinase sites. By removing the phosphorylated peptide by an appropriate ubiquitin carboxyl-terminalhydrolase, one can readily sequence the phosphorylated peptide.

The Ub-cRAS (Cys-Val-Leu-Ser) (SEQ ID NO:5) extension is an excellent substrate for identifying farnesyl-protein transferase (FPT) activities as demonstrated by using Xenopus egg extract and rabbit reticulocyte lysate. Extracts prepared from these sources can be incubated with Ub-cRAS (Cys-Val-Leu-Ser) in the presence of $^3$H-farnesyl pyrophosphate (FPP). After terminating the reactions, such as with SDS-PAGE buffer, the samples can be electrophoresed, such as on a 10-20% acrylamide gel and an autoradiogram taken. The resulting autoradiogram demonstrates that FPT activity in both extracts transferred tritium from $^3$H-FPP to Ub-cRAS (Cys-Val-Leu-Ser). It is also found that the extent of Ub-cRAS (Cys-Val-Leu-Ser) farnesylation is proportional to enzyme concentration in the extracts thereby demonstrating that the present invention provides a quantitative assay for FPT. Additionally it has been found that farnesylated Ub-cRAS serves as a substrate for identifying carboxyl methyltransferase activity. When Ub-cRAS (Cys-Val-Leu-Ser) is incubated in Xenopus egg extracts, with or without unlabeled FPP (1 nmole), and added S-adenosylmethionine (AdeMet) as the labeled methyl donor and the reaction mixture is analyzed, e.g. by SDS-PAGE followed by fluorography, the resulting autoradiogram demonstrates that Ub-cRAS (Cys-Val-Leu-Ser) becomes labeled by [$^3$H-methyl]AdeMet only when excess FPP is also added to the reaction mixture.

While the present invention focuses on substrates for assaying protein kinase, FPT and carboxyl methyltransferase activities, one skilled in the art can also design peptide extensions for specific assays of other known enzymes or specificity studies on newly discovered enzymes. By judicious choice of oligonucleotides that encode sets of related peptide extensions at the C-terminus of ubiquitin, one can prepare multiple potential enzyme substrates in a single transformation experiment. These molecules can, in turn, be used to search for novel enzymes or to assay the substrate specificity of newly discovered enzymes. These enzymes are important in cell division. It is very likely that clinical tests for such enzymes will be developed to monitor the progress of tumors or to screen for genetic defects.

DETAILED DESCRIPTION OF THE INVENTION

The examples illustrated below show that Ub-cRAS (Cys-Val-Leu-Ser) extensions provide suitable substrates for assaying FPT and carboxyl methyltransferase which modify the C-terminus of the Ha-RAS protein. Data in Examples 4-7 show that Ub-cRAS (Cys-Val-Leu-Ser) (SEQ ID NO:5), can accept $^3$H-farnesyl from $^3$H-FPP and, in the presence of excess unlabeled FPP, $^3$H-methyl groups from S-adenosylmethionine. Gutierrez et al., *EMBO J.* (1989), 8:1093-11096; Marcus et al.; Stimmel et al., *Biochemistry* (1990), 29:9651-9659 and Hancock et al., *EMBO J.,* (1991), 10:641-646 all provide evidence that removal of the three terminal residues (Val-Leu-Ser) of the Ha-RAS protein is needed for carboxyl methylation, therefore the data in Example 7 indicate that the Ub-cRAS (Cys-Val-Leu-Ser) extension is also suitable substrate for the processing protease since the methylation reaction could not proceed unless a protease had first cleaved the three C-terminal residues of a farnsylated substrate leaving the sulfur reactive cysteine in a terminal position for reaction with the $^3$H-methyl groups from S-adenosylmethionine. Although not shown herein it has been observed that Ub-cRAS can accept $^{14}$C-palmitate from palmitic acid in Xenopus egg extract. It is therefore believed that Ub-cRAS extensions are subjected to all known modifications of the C-terminus of RAS which logically leads to the conclusion that the C-terminus of the Ub-cRAS extension functions essentially the same as the C-terminus of the Ha-RAS protein but possesses all of the advantages characteristic of ubiquitin.

Reiss et al., *Cell,* (1990), 62:81-88, Goldstein et al., *J. Biol. Chem.,* (1991), 266:15575-15578, Kim et al., *Mol. Cell. Biol.,* (1990), 10:5945-5949, Reiss et al., *Proc. Natl. Acad. Sci. USA,* (1991), 88:732-736 and Tan et al., *J.*

Biol. Chem., (1991), 266:10719–10722 show that small peptides can be used in assays for lipid modification. In view of this, one might question the advantage of utilizing ubiquitin over the use of a small peptide alone and/or be concerned about potential complications resulting from the N-terminal ubiquitin moiety. As enzyme substrates Ub-peptide extensions offer several distinct advantages over short peptides. First, Ub-peptide extensions are extremely inexpensive to synthesize in large quantities. The single stranded procedure outlined in FIG. 1 substantially reduces the initial cost for peptides on a per residue basis. Expenses for subsequent rounds of synthesis are almost reduced to the price of the bacterial growth medium employed. Second, Ub-peptides can, in certain cases, be purified from bacterial extracts by simple acid extraction. Third, some assays may require electrophoretic analysis for accurate quantitation. For example, the methyl transferase activity detected in Example 7 is not specific to the Ub-cRAS extension. The fact that Ub-peptides migrate on SDS-Page gels in a region (~9K) virtually devoid of other proteins reduces greatly any possible confusion from endogenous proteins that may also become modified. Fourth, the presence of Ub at the N-terminus of the peptide substrate is probably crucial for product capture by PDVF or other similarly utilized membranes. While Ub-cRAS (Cys-Val-Leu-Ser) peptide and the cRAS peptide alone were not directly compared in membrane binding, it is believed that farnesylated short peptides will adsorb to PDVF or other membranes much less well than Ub-peptide extensions. The above advantages far outweigh any potential complications resulting from the presence of ubiquitin at the peptide's N-terminus.

Although the thrust of the invention is directed to the use of Ub-peptides as enzyme substrates, several observations were also made which are relevant to the biochemistry of RAS modification. In Example 7 it is shown that the Ub-cRAS (Cys-Val-Leu-Ser) becomes methylated in a FPP stimulated reaction whereas a Ub-cRAS (Ser-Val-Leu-Ser) (SEQ ID NO:9) variant, where (Ser-Val-Leu-Ser) is the one letter amino acid code for the terminal four amino acids Ser-Val-Leu-Ser in the peptide extension, does not. These results indicate that in Xenopus egg extract Ub-cRAS (CVLS) is first farnesylated, then processed by proteolysis and the Cys residue bearing the C-terminal carboxyl group is methylated. Both the failure of the serine variant, Ub-cRAS (Ser-Val-Leu-Ser) (SEQ ID NO:9) to become carboxyl methylated and the absence of Ub-cRAS (Cys-Val-Leu-Ser) (SEQ ID NO:5) methylation when excess FPP is omitted indicates that farnesylation precedes methylation.

DETAILED DESCRIPTION OF PREFERRED EMBODIMENTS AND BEST MODE

Materials

Casein, α-casein, bovine ubiquitin, ATP (adenosine triphosphate), GTP (guanosine triphosphate), creatine phosphokinase, and phosphocreatine were obtained from Sigma Chemical Co. Coomassie protein assay reagents were purchased from Pierce Chemical Co. Acrylamide and bisacrylamide were purchased from Bio-Rad. Q-Sepharose was obtained from Pharmacia. [$\alpha^{35}$S]ATP, [$\gamma$-$^{32}$P]ATP, and [$\gamma^{32}$P]GTP were purchased from Amersham. The ubiquitin coding gene in pNMHub and the E. coli expression strain AR13 were obtained from Smith, Kline and French. $^3$H-Farnesyl pyrophosphate (20 Ci/mmol), [$^3$H-methyl] AdeMet (10 Ci/mmol), and En$^3$Hance Spray were purchased from DuPont-New England Nuclear. Muta-Gene M13 in vitro mutagenesis kit and Sequenase Version 2.0 were obtained from BioRad and United States Biochemical. Amplify was purchased from Amersham. Unlabeled FPP was obtained at The University of Utah. Immobilon-p$^{SQ}$ PVDF membrane was purchased from Millipore.

Extract Preparation

Containing Casein Kinase II

Rabbit reticulocyte lysate was prepared and chromatographed on Fractogel DEAE-650S using a 0.1 to 0.5 m KCl gradient as described by Hough et al., J. Biol. Chem., (1987), 262:8303–8311. Two peaks of casein kinase II (CKII) activity were observed; one form of the enzyme eluted at concentrations between 0.15 and 0.2M; and the other eluted between 0.25 and 0.35M KCl. The latter fractions were used in all experiments requiring partially purified reticulocyte CKII. Crude extracts were also prepared from rat liver, HeLa cells and Xenopus eggs. Rat liver was homogenized with 2.5 vol of 50 mM Tris-HCl, pH 7.6, containing 1 mM EDTA and 1 mM DTT. The homogenate was centrifuged for 1 h at 15,000 g and the supernate was used as liver extract. HeLa cells ($10^7$) were lysed in 100 μl of 10 mM Tris-HCl, pH 7.6, containing 0.25% Triton X-100 and 1 mM DTT. The lysate was used as HeLa extract. Xenopus egg extract was prepared as described by Murray et al., Nature, (1989), 339:275–280.

Containing Farnesyl-Protein Transferase

Rabbit reticulocyte lysate was prepared as described by Hough et al., J. Biol. Chem., (1986), 261:2400–2408 and was chromatographed on a Q-Sepharose column (1×10 cm) using a 0 to 0.5.M NaCl gradient in 20 mM Tris-HCl (pH 7.6), 5 mM MgCl$_2$, and 1 mM DTT. A single peak of farnesyl-protein transferase activity was detected among those proteins eluting between 0.3.M and 0.34M NaCl. Fractions containing FPT activity were pooled, concentrated through PM10 membrane, and subjected to a Sephacryl S-300 column (1×90 cm) equilibrated with 20 mM Tris (pH 7.6), 5 mM MgCl$_2$, 1 mM DTT, and 0.1M NaCl. Xenopus egg extract was prepared as described by Murray et al., supra.

EXAMPLE 1

Figure 1:
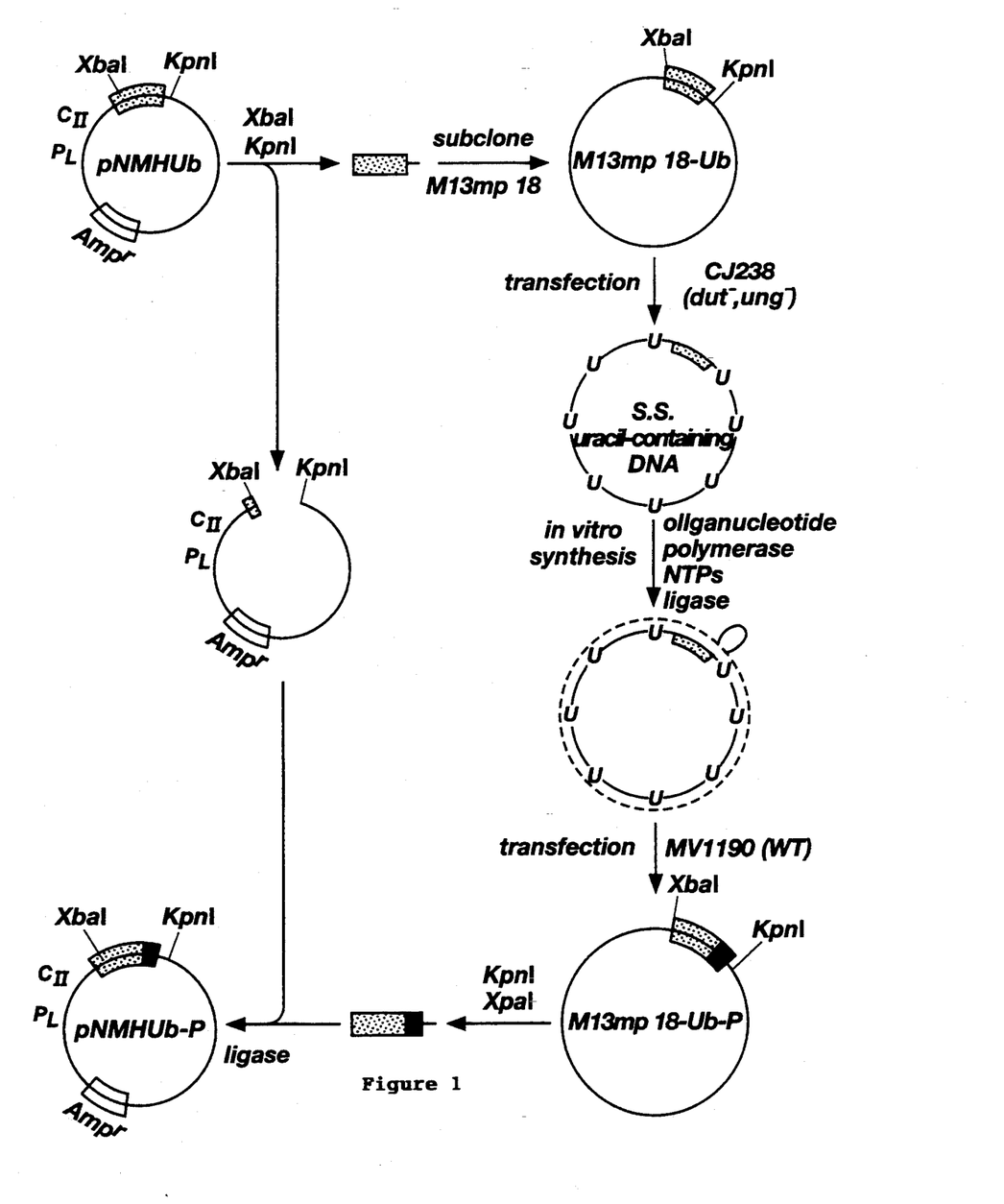
FIG. 1 is a schematic representation for cloning the recombinant plasmid (pNMDUb-P) of Ub-cRAS peptide extension protein using oligonucleotide-mediated "loop-in" mutagenesis. The same representation is also applicable for preparation of the various Ub-PEST and Ub-AEX peptide extensions.

Construction of Expression Ub-cRAS Vectors by Oligonucleotide-Mediated "Loop-in" Mutagenesis The construction of Ub-cRAS extensions in M13 as described herein is shown diagrammatically in FIG. 1. The ubiquitin coding gene in pNMHub was digested with XbaI and KpnI and the resulting fragment was subcloned into the polylinker site of M13mp18 using standard recombinant DNA techniques as disclosed by Sambrook et al., Molecular Cloning: A Laboratory Manual, 2nd Ed. (1989), Cold Spring Harbor Laboratory, Cold Spring Harbor, N.Y. This construct (M13mp18Ub) was used to prepare the single-stranded, uracil-containing template DNA. A synthetic oligonucleotide (AGACTAAGAGGTGGTCCCGGATG-CATGTCTTGTAAATGTGTACTATCATGAGG-TACCGAGCTC) (SEQ ID NO:10) was designed to add eleven amino acids, the residues Pro-Gly-Cys-Met-Ser-Cys-Lys-Cys-Val-Leu-Ser, (SEQ ID NO:11) to the carboxyl terminus of ubiquitin, and oligonucleotide-mediated "loop-in" mutagenesis was performed according to the methods of Kunkel et al., *Methods Enzymol.* (1987), 154:367–382 using the BioRad mutagenesis kit. Detection of the desired mutation (M13mp18Ub-p) was performed by sequencing the resulting phage DNA's via dideoxy chain termination method of Sanger et al., *Proc. Nat. Acad. Sci. USA* (1974), 74:5463–5467. The mutated fragment was removed by XbaI and KpnI from RF DNA of the phage, ligated into pNMHUb, and then transformed into the wild type lysogen, MM294CI+. After confirming the correct transformants by double-strand DNA sequencing, the mutated plasmid was transformed into the expression strain, AR13, which contains a temperature-sensitive λ repressor. Another single-stranded, uracil-containing template DNA was prepared from M13mp18Ub-p, and site-directed mutagenesis was performed to substitute the last cysteine in the Ha-RAS extension by serine using the mutagenic primer (TCTTGTAAATCAGTACTATCAT) (SEQ ID NO:12) to add the residues Pro-Gly-Cys-Met-Ser-Cys-Lys-Ser-Val-Leu-Ser (SEQ ID NO:13) to the carboxyl terminus of ubiquitin.

EXAMPLE 2

Expression and Isolation of Ub-cRAS Peptide Extensions

Ub-peptide extensions were expressed as described by Rechsteiner et al., copending patent application Ser. No. 07/420,544 filed Oct. 12, 1989 and Yoo et al., *J. Biol. Chem.* (1989) 264:17,078–17,083. *E. coli* AR13 cells transformed with pNMHUb-cRAS were grown at 32° C. to an O.D.$_{600}$=0.8, and rapidly shifted to 42° C. After three hours, cells were harvested by centrifugation and washed once with ice-cold water. The cell pellet was resuspended in 25 mM sodium citrate (pH 3;5) after a freeze-thaw, allowed to stand at room temperature for one hour with occasional stirring, and centrifuged at 20,000×g for 30 min. Protein in the supernate was concentrated by Amicon filtration using a YM5 membrane. Samples were then analyzed on a 10–20% SDS-PAGE gel and visualized by staining with Coomassie Brilliant Blue. Purity of the Ub-cRAS extension proteins was generally greater than 90%.

The Ub-cRAS extensions obtained were of formulas:
Ub-cRAS (Cys-Val-Leu-Ser) (SEQ ID NO:5)
Ub$_{73}$-Arg-Gly-Gly-Pro-Gly-Cys-Met-Ser-Cys-Lys-Cys-Val-Leu-Ser and
Ub-cRAS (Ser-Val-Leu-Ser) (SEQ ID NO:9)
Ub$_{73}$-Arg-Gly-Gly-Pro-Gly-Cys-Met-Ser-Cys-Lys-Ser-Val-Leu-Ser
where Ub73 stands for the N-terminal 73 amino acids from ubiquitin.

EXAMPLE 3

Expression and Isolation of Ub-PEST and Ub-AEX Peptide Extensions

Four ubiquitin-peptide extension proteins, Ub-PEST1 (SEQ ID NO:2), Ub-PEST4 (SEQ ID NO:3), Ub-PEST2 (SEQ ID NO:6), and Ub-PEST3 (SEQ ID NO:7) were prepared as in the manner described in Examples 1 and 2, and an uncleavable ubiquitin-peptide extension protein (Ub-AEX) (SEQ ID NO:4) was prepared by minor modifications of the reported method of Yoo et al., supra. That the recombinant plasmid encoded a noncleavable ubiquitin peptide was confirmed both by sequencing the recombinant plasmid and by incubation of the expressed protein in crude extracts containing a ubiquitin carboxyl-terminal hydrolase. The expressed ubiquitin peptide extensions were isolated as described previously by Yoo et al., supra, except that Q-Sepharose was substituted for DEAE-cellulose during ion-exchange chromatography.

EXAMPLE 4

Farnesylation of Ub-cRAS (CVLS) Peptide In Vitro

The standard reaction mixture for farnesyl-protein transferase, adapted from the procedure of Schaber et al., *J. Biol. Chem.*, (1990), 265:680–685 was utilized. Ub-cRAS fusion protein or Ub (1 nmol) was incubated with rabbit reticulocyte lysate (1.0 μl), Xenopus egg extract (1.0 μl) or partially purified farnesyl-protein transferase (1.0 μl) in a final volume of 20 μl containing the following components: 50 mM NaHepes (pH 7.5), 5 mM MgCl$_2$, 5mM DTT, 12.5 pmol (0.25 μCi) of [$^3$H]FPP (20 Ci/mmol). After incubation at 25° C. for 30 min, reactions were quenched by adding 5 μl of 5×SDS-sample buffer. After boiling the sample for 3 min, proteins were separated on a 10–20% gradient SDS-PAGE by the method of Laemmli, *Nature*, (1970), 227:680–685, and incorporated tritium was determined by autoradiography after fluorographic enhancement with Amplify (Amersham).

The Ub-cRAS (Cys-Val-Leu-Ser) extension (SEQ ID NO:5) proved to be an excellent substrate for farnesyl-protein transferase (FPT) activities in both Xenopus egg extract and rabbit reticulocyte lysate. The resulting autoradiogram confirmed that an activity in both Xenopus egg extract and rabbit reticulocyte lysate extracts transferred tritium from $^3$H-FPP to Ub-cRAS (Cys-Val-Leu-Ser). However the native ubiquitin molecule not extended by the cRAS peptide at the C-terminus and the Ub-cRAS (Ser-Val-Leu-Ser) (SEQ ID NO:9) variant, containing serine in the place of cysteine, were both inactive as substrates for FPT. Moreover, the extent of Ub-cRAS (Cys-Val-Leu-Ser) farnesylation was found to be proportional to enzyme concentration thereby providing a quantitative assay for FPT.

EXAMPLE 5

Because it is cumbersome to use gel electrophoresis in enzymatic assays as described in Example 4, an alternate method of capturing the farnesylated Ub-cRAS was devised using a PVDF (polyvinylidenefluoride) membrane. Ub-cRAS (Cys-Val-Leu-Ser) (SEQ ID NO:5) was incubated with 0.5 μl of Xenopus egg extract using the same farnesyl-protein transferase reaction mixture as described in Example 3 for 30 min at 25° C. and the reaction was terminated by adding 40 μl of 40% methanol plus 1% SDS. The reaction mixture was then transferred onto a Immobilon PVDF membrane (microporous polyvinylidenefluoride membrane with a modified structure for increased protein binding) using a VacuSlot-VS. The membrane was stained with Coomassie Brilliant Blue R-250 and destained in 40% methanol plus 10% acetic acid, prior to measuring the radioactivity in each band by liquid scintillation spectroscopy. Incorporation of tritium was also visualized by fluorography of the membrane after enhancement using En$^3$-Hance Spray. The radioactivity detected on each of the bands, in counts per minute (cpm), by the liquid scintillation spectroscopy is given in Table 1.

TABLE 1

| Substrate | Counts per Minute |
|---|---|
| None | 80 |
| Ub-cRAS CVLS (SEQ ID NO:5) | 3908 |

TABLE 1-continued

| Substrate | Counts per Minute |
| --- | --- |
| Ub-cRAS SVLS (SEQ ID NO:9) | 109 |
| Ub | 103 |

The data in Table 1 confirm that adsorption of farnesylated Ub-cRAS (Cys-Val-Leu-Ser) to Immobilon provides a highly discrimination assay for FPT. The native ubiquitin substrate and the serine modified variant Ub-cRAS (Ser-Val-Leu-Ser) provided activity only slightly higher than the background found on the membrane alone when no substrate was added.

EXAMPLE 6

To determine whether the membrane binding assay demonstrated in Example 4 is as quantitative as SDS-PAGE analysis of reaction products as shown in Example 3 a direct comparison was made of the two methods using Ub-cRAS (Cys-Val-Leu-Ser) (SEQ ID NO:5) as the substrate.

Ub-cRAS was incubated with Xenopus egg extract under standard conditions as given above. The reaction was stopped by adding 2×SDS-PAGE sample buffer after 15, 30, 45 and 60 minutes. Half of the reaction mixture was transferred onto the PVDF membrane above according to the procedure of Example 5 and the other half was subjected to 10-20% gradient SDS-PAGE according to Example 3. Autoradiograms of the gel and the membrane were obtained after fluorographic enhancement and visually were found to be substantially identical. The radioactivity in each band from the gel and from the PDVF membrane was measured with a scintillation counter and plotted against incubation time. When compared in tabular form the results, in approximate counts per minute, are given in Table 2.

TABLE 2

| Time | Counts per Minute (cpm) | |
| --- | --- | --- |
| | Gel | Membrane |
| 15 | 1030 | 980 |
| 30 | 2000 | 1850 |
| 45 | 2700 | 2400 |
| 60 | 3200 | 2800 |

According to the results from visual analysis of the autoradiograms and the data given in Table 2, the much easier membrane binding assay is of equally as sensitive as the electrophoretic procedure, and both methods provide quantitative estimates of FPT activity.

As stated above, there was no direct comparison between the Ub-cRAS (Cys-Val-Leu-Ser) peptide and the cRAS peptide alone in membrane binding. However, based on the properties of the shorter cRAS peptide it is thought that farnesylated short peptides will adsorb to PVDF membranes much less well than Ub-cRAS peptide extensions.

Also, it is believed that other membranes may be utilized other then PVDF. For example, membranes which may be surface modified to contain amino groups to enhance binding capabilities are particularly suitable. Representative polymers include suitable hydrocarbons, fluorocarbons, chlorofluorocarbons, vinyl alcohols and vinyl chlorides and copolymers and blends thereof. In addition to polyvinylidenefluoride (PVDF), other exemplary polymers include polypropylene (PP), polyethylene (PE), polytetrafluoroethylene (PTFE), polyvinylchloride (PVC), polyfluoroethylene-propylene (PFEP), ethylenevinylalcohol (EVAL), and polyethylenechlorotrifluoroethylene (PECTFE) and blends and copolymers thereof.

Farnesylation is just the first of several modifications to which the C-terminus of RAS is subjected. As referenced above, others have presented evidence that removal of the last three amino acids from RAS is a factor in allowing methylation of the carboxyl group at the farnesylated cysteine terminus. Hancock et al., Cell, (1989), 57:1167-1177 provide evident that some RAS termini are palmitoylated as well. Stephenson et al., J. Biol. Chem., (1990), 265:16248-16254, examined the carboxyl methylation reaction using farnesylated peptides as substrates. Although the assay disclosed is rigorous and quantitative, it is somewhat inconvenient due to the necessity of capturing gaseous methanol after methylester hydrolyses. The present invention represents a substantial improvement over this technique in that farnesylated Ub-cRAS (Cys-Val-Leu-Ser) has been shown to serve as a substrate for the carboxyl methyltransferase allowing for a simple assay technique as shown in the following example.

EXAMPLE 7

Carboxyl Methylation of Ub-cRAS (Cys-Val-Leu-Ser) Peptide in Vitro

Xenopus egg extract (0.5 μl) was incubated with Ub-cRAS (Cys-Val-Leu-Ser) (SEQ ID NO:5) and [$^3$H-methyl] AdeMet (5.5 uci), as the labeled methyl donor, in the presence or absence of 1 nmol of unlabeled FPP at 25° C. for 30 minutes. Reactions were stopped by adding SDS sample buffer analyzed by 10-20% gradient SDS-PAGE followed by fluorography. The resulting autoradiogram showed that Ub-cRAS (Cys-Val-Leu-Ser) became labeled by [$^3$H-methyl]AdeMet only when excess FPP was also added to the reaction mixture. The serine variant, Ub-cRAS (Ser-Val-Leu-Ser), (SEQ ID NO:9), did not accept methyl groups presumably because it cannot be farnesylated.

In summary, it is demonstrated above that the Ub-cRAS (Cys-Val-Leu-Ser) peptide (SEQ ID NO:5) is an excellent substrate for identifying and assaying farnesyl-protein transferase (FPT) activities in Xenopus egg extract and rabbit reticulocyte lysate and that the farnesylated Ub-cRAS is, in turn, also an excellent substrate for assaying for the carboxyl methyltransferase enzyme. It is further demonstrated that adsorption of farnesylated Ub-cRAS to a suitable membrane provides a highly discrimination assay for FPT which is easier and as sensitive and quantitative as SDS-PAGE analysis.

When applicable in the ensuing examples gel electrophoresis and autoradiography were carried out as follows. SDS-PAGE was performed by the methods of Laemmli, supra, except that the Tris concentrations were increased in the separating gel (0.75M) and running buffer (50 mM) to improve the resolution of small proteins in the manner of Fling et al., Anal. Biochem., (1986), 155:83-88. The sample buffer contained 100 mM Tris-HCl, pH 6.8, 3% SDS, 5% 2-mercaptoethanol, 10% glycerol, and 0.2% bromophenol blue. Autoradiograms were obtained by exposing dried gels to Kodak X-ray film.

EXAMPLE 8

Casein kinase II activity was determined by the incorporation of $^{32}$P into casein or ubiquitin-peptide extension proteins. Partially purified casein kinase II or crude extracts were incubated without a substrate, or with a substrate selected from the group consisting of 25 μg α-casein, 25 μg bovine ubiquitin, or 10 μg each of Ub-PEST1 (SEQ ID NO:2), Ub-PEST4 (SEQ ID NO:3), Ub-PEST 2 (SEQ ID NO:6), and Ub-PEST3 (SEQ ID NO:7) in a final volume of 50 μl at 30° C. for 10 min in the presence of 50 mM Tris-HCl, pH 7.2, 10mM MgCl$_2$, 100 mM NaCl, and 100 μM [γ-$^{32}$P]GTP or [γ-$^{32}$P] ATP (1000–3000 cpm/pmol; Amerisham Corp.).

Reactions were initiated by adding enzyme and terminated in three different ways. An aliquot of the reaction mixture was spotted on Whatman P81 paper. The filter paper was then washed three times in 75 mM H$_3$PO$_4$ and dried, and the bound radioactivity was measured by liquid scintillation spectrometry in the manner of Glass et al., *Anal. Biochem.*, (1978), 87:566-575. Alternatively, an aliquot of the completed reaction mixture was added to 0.9 ml of 1% BSA in water followed by 0.1 ml of 100% trichloroacetic acid (TCA). After centrifugation in a microfuge for 15 min, the pellet was resuspended in fluor and the precipitated $^{32}$P was measured by liquid scintillation spectrometry. In the third assay, an aliquot of the reaction mixture was added to 2×SDS sample buffer. The proteins were then separated on 10-20% gradient SDS-PAGE gels. After an autoradiogram was obtained, the incorporated $^{32}$PO$_4$ was measured as Cerenkov radiation from individual gel slices.

In each assay it was qualitatively shown that there was phosphorylation of the α-casein, Ub-PEST1 (SEQ ID NO:2) and Ub-PEST4 (SEQ ID NO:3) but no phosphorylation was present in the sample with no substrate, or in the presence of the bovine ubiquitin. Also, even through they contain as many serine residues as the Ub-PEST1 and Ub-PEST4 substrates, the Ub-PEST2 (SEQ ID NO:6) and Ub-PEST3 (SEQ ID NO:7) substrates showed no evidence of phosphorylation.

EXAMPLE 9

The correspondence between the filter binding assay, the acid-precipitation procedure and the SDS-PAGE followed by autoradiography was determined by following the kinetics of phosphorylation of Ub-PEST1 (SEQ ID NO:2) by partially purified casein kinase II. CKII (1 μg) was incubated with 200 μg of Ub-PEST1 at 30° C. in 0.5 ml of the reaction buffer described in Example 8. Aliquots were taken at 5, 15, 30, 60 and 90 minutes of incubation time and the phosphate incorporation into the substrate was measured by the filter paper, TCA precipitation and SDS-PAGE and autoradiography techniques utilized in Example 8. The filter paper and TCA precipitation assays showed close correspondence in quantitative phosphorylation indicating that all three methods are suitable assay techniques.

EXAMPLE 10

Eucaryotic cells contain specific proteases for cleaving peptide extensions from ubiquitin as shown by Mayer et al., *Biochemistry*, (1989), 28:166-177. The existence of such enzymes presents a possible complication in the use of ubiquitin fusion peptides as kinase substrates, particularly when crude extracts are surveyed.

To circumvent this potential problem, the Ub-AEX peptide extension (SEQ ID NO:4) was constructed in which residues 74-76 of ubiquitin, Arg-Gly-Gly, were changed to Gln-Gly-Ala and these residues were followed by Met-Glu-Ala-Ser-Glu-Glu-Glu-Glu-Glu-Phe (SEQ ID NO:8). Altering the last three residues in ubiquitin did not greatly reduce the yield of peptide extension upon induction of *E. coli* but this modification did produce an extension protein, Ub-AEX, that cannot be cleaved by the cell's normal ubiquitin carboxyl-terminal hydrolase.

The following tests were conducted to determine whether the noncleavable Ub-AEX (SEQ ID NO:4) extension, native ubiquitin, and Ub-PEST1 (SEQ ID NO:2) would serve as kinase substrates in crude extracts from HeLa Cells, mouse liver or Xenopus eggs.

The protein substrates (25 μg of each) were added to crude extracts containing [γ$^{32}$P]ATP and, after 10 min of incubation at 30° C., the reaction mixtures were analyzed on SDS-PAGE gradient gels by staining with Coomasie blue stain followed by autoradiography. The Coomassie blue-stained gel showed that all three crude extracts, i.e. HeLa Cells, mouse liver and Xenopus eggs, contained hydrolyase enzymes capable of cleaving the peptide extension from Ub-PEST1. In each case, the Ub-PEST1 lane contained two major protein bands with molecular weights between 6000 and 9000 Da. The upper band corresponds to the intact ubiquitin carboxyl extension whereas the lower band is processed free ubiquitin. It is also clear that changing arginine-74 of ubiquitin to glutamine and glycine-76 to alanine, i.e. Ub-AEX, prevented removal of the peptide extension since the Ub-AEX lane of each crude extract contains only the intact and, hence, noncleavable, Ub-AEX.

The autoradiograms taken of each extract allowed several conclusions to be drawn from the pattern of the phosphorylated products obtained. First of all, ubiquitin was shown not to be phosphorylated in any of the crude extracts as shown by the absence of phosphate incorporation into proteins of M.<10,000. Comparing the relative $^{32}$PO$_4$ incorporation into the cleavable, Ub-PEST1, and noncleavable, Ub-AEX, ubiquitin extension proteins, it was demonstrated that both are substrates for a kinase(s), presumably casein kinase II, present in each crude extract. This was not immediately apparent in samples from rat liver extract which exhibits low levels of kinase activity toward the ubiquitin extensions. But longer exposure of the gel reveals that noncleavable Ub-AEX was also phosphorylated in liver extract. Because Ub-PEST1 is partially cleaved to ubiquitin and the free PEST1 peptide, it was suprising to observe greater net $^{32}$PO$_4$ incorporation into Ub-PEST1 relative to the noncleavable Ub-AEX. An explanation for this apparent discrepancy is provided by kinetic analyses presented in Example 12 below.

EXAMPLE 11

It is often difficult to measure a specific protein kinase in crude extracts accurately because endogenous substrates for other kinases produce a high background of phosphorylated proteins. However, the stability of ubiquitin at high temperatures provides a means that the background problem can be circumvented simply by heating the completed reaction mixture and centrifuging away the denatured proteins. High-temperature denaturation did indeed prove an effective way to reduce background as demonstrated by the following tests.

Ubiquitin, Ub-PEST1 (SEQ ID NO:2) and Ub-AEX (SEQ ID NO:4) (25 μg) were incubated with frog egg extract or partially purified rabbit reticulocyte CKII at 30° C. for 10 minutes in 10 μl of the $^{32}$P containing reaction buffer as in the above examples. A portion of each completed reaction was heated to 85° C. for 10 minutes, cooled on ice and clarified by centrifugation at 15,000 g for 15 min. The samples were then analyzed by autoradiography after separation on 10-20% gradient SDS-PAGE gels. Comparison of Coomasie blue-stained gels of heated and unheated extracts show that heating the Xenopus egg extract markedly reduced the solubility of endogenous proteins while most of the ubiquitin and the Ub-PEST1 and Ub-AEX peptide extensions remained in solution. The same finding was found in the corresponding autoradiograms of the same gels which document the efficient removal of phosphorylated proteins other than the Ub-PEST1 and Ub-AEX peptides.

Partially purified kinase preparations from partially purified rabbit reticulocyte may also contain endogenous substrates and competing kinases that can complicate enzyme assays. The stained gels and autoradiograms from this extract demonstrate that heating is equally effective for solutions containing lower levels of endogenous proteins. Quantitative analyses of the distribution of the $^{32}P$ isotope in the Ub-AEX lanes from unheated and heated extracts revealed that heating reduced labeled endogenous proteins from 17% to less than 2%. This was accompanied by a modest 19% loss of phosphorylated Ub-AEX peptide.

EXAMPLE 12

The data presented so far demonstrate qualitatively that Ub-peptide extensions can serve as protein kinase substrates. Kinetic studies were performed to determine the relative efficiency of peptide extensions as substrates for reticulocyte CKII. Partially purified CKII (100 ng) was incubated at 30° C. for 5 minutes with different amounts of casein, Ub-PEST1 (SEQ ID NO:2) and Ub-AEX (SEQ ID NO:4) as substrates. The incorporated $^{32}PO_4$ was measured by acid precipitation or by SDS-PAGE plus autoradiography. Accordingly, it was found that Ub-PEST1 ($K_m=27$ μM) is virtually equivalent to casein ($K_m=22$ μM). By contrast, the shorter noncleavable extension, Ub-AEX, has a significantly greater $K_m$ (133 μM) presumably because the body of the ubiquitin molecule prevents easy access of the peptide to the active site of casein kinase II. This may explain why the cleavable UB-PEST1 incorporated more $^{32}PO_4$ than the noncleavable Ub-AEX in the experiments shown in Example 10.

EXAMPLE 13

Ubiquitin-peptide extensions offer unique opportunities for locating phosphorylated residues in sequences containing several potential kinase sites. This examples demonstrates that it is possible to remove the peptide extension by specific ubiquitin carboxyl-terminal hydrolase, thereby permitting easy sequencing of the phosphorylated peptide. To determine whether phosphorylated peptides can be cleaved from ubiquitin, a Ub-PEST1 (SEQ ID NO:2) sample, phosphorylated by partially purified casein kinase II, was incubated with ubiquitin carboxyl terminal hydrolase, after removal of endogenous proteins and free [$^{32}P$]-GTP by heating and gel filtration, respectively. A more detailed description of this procedure is as follows.

After phosphorylation of substrates, the reaction mixtures were incubated at 85° C. for 10 min, cooled on ice, and centrifuged at 15,000g for 15 min. Free [$^{32}P$]-GTP in the supernate was then removed by gel filtration on Sephadex G-25 equilibrated with 50 mM Tris-HCl, pH 7.6, and 5 mM DTT. The fractions containing protein were pooled, incubated with ubiquitin carboxyl-terminal hydrolase at 37° C. for 10 min, and analyzed by autoradiography after separation on 10-20% gradient SDS-PAGE gels. Ubiquitin carboxyl-terminal hydrolase was partially purified as described Yoo et al., supra or was a generous gift from Dr. K. Wilkinson of Emory University. The autoradiogram confirmed that ubiquitin carboxyl terminal hydrolase removed the PEST1 peptide extension even when that extension contained phosphoserine.

It should be noted that the ubiquitin carboxyl-terminal hydrolase utilized in this example is specific to the removal of short peptide extensions from ubiquitin where ubiquitin is the dominant part of the molecule but does not function to cleave long peptides or proteins which are more dominant than ubiquitin. Additionally, the ubiquitin carboxyl terminal hydrolase is able to remove precisely the peptide extension without further cleaving the released peptide as demonstrated by Yoo et al., supra, and Mayer et al., supra.

The data presented above demonstrate that ubiquitin-peptide extensions are convenient substrates for the assay of various enzymes which react with the peptide extension portion of these substrates. However, the success of the invention depends on the properties of the ubiquitin molecule which possesses characteristics that make it particularly valuable as a carrier of peptides containing specific enzyme reaction sites. Another important advantage of ubiquitin-peptide extensions in certain assay techniques is the availability of enzymes able to remove precisely the peptide extension without further cleaving the released peptide. Since such enzymes are active against phosphorylated peptide extensions in protein kinase assays, studies requiring analysis of the exact site of phosphorylation are made possible.

While the data presented are focused on substrates for casein kinase II, farnesyl-protein transferase and carboxyl methyl transferase, one skilled in the art could also design peptide extensions for specific assay of other enzymes such as known kinases, e.g. PKC or $Ca^{2+}$-/Cam-dependent kinases, specificity studies on newly discovered kinases or the assay of other methyl or lipid transferases. By judicious choice of oligonucleotides that encode sets of related peptide extensions at the C-terminus of ubiquitin, one can prepare multiple potential enzyme substrates in a single transformation experiment. These molecules can, in turn, be used to search for novel enzymes within known classes, such as kinases or to assay the substrate specificity of newly discovered enzymes. The usefulness of the invention in relation to enzyme assay techniques is limited only by the ability of the peptide extension to interact with the enzyme and be identified qualitatively or quantitatively by suitable recognition techniques. The invention is therefore limited only by the scope of the following claims.

---

We claim:

1. A method for assaying for enzymes that modify peptide chains which comprises,
   (a) providing a substrate comprising a ubiquitin-peptide extension wherein said ubiquitin-peptide extension contains a sequence known to be modified in the presence of an enzyme being assayed for;
   (b) incubating a test sample with said ubiquitin-peptide extension in a reaction mixture solution containing one or more reagents needed for said enzyme to modify said peptide extension when said enzyme is present;
   (c) terminating said incubation and analyzing the reaction mixture solution for the presence of said ubiquitin-peptide extension in modified form.

2. The method of claim 1 wherein said enzyme being assayed for is selected from the group consisting of protein kinases and enzymes which modify the C-terminal end of the Ha-RAS protein.

3. The method of claim 2 wherein said enzyme being assayed for is an enzyme which modifies the C-terminal end of the Ha-RAS protein.

4. The method of claim 3 wherein said enzyme being assayed for is farnesyl-protein transferase.

5. The method of claim 4 wherein said ubiquitin-peptide extension has the formula (SEQ ID NO:5):
Ub$_{73}$-Arg-Gly-Gly-Pro-Gly-Cys-Met-Ser-Cys-Lys-Cys-Val-Leu-Ser
where Ub$_{73}$ represents the N-terminal 73 amino acids from ubiquitin.

6. The method of claim 5 wherein said reagent needed to modify said peptide extension when said enzyme is present is farnesyl pyrophosphate (FPP) and said modification is farnesylation of said peptide extension.

7. The method of claim 6 wherein said FPP is tritium labeled as $^3$H-farnesyl pyrophosphate ($^3$H-FPP).

8. The method of claim 7 wherein said analysis of the reaction mixture is performed by terminating said incubation with an effective amount of detergent, separating said ubiquitin-peptide extension in modified farnesylated form from said solution by electrophoresis followed by detection for the presence of tritium in the farnesylated ubiquitin-peptide extension.

9. The method of claim 8 wherein said detection is accomplished by autoradiography.

10. The method of claim 7 wherein said analysis of the reaction mixture is performed by terminating said incubation with an effective amount of detergent, separating said ubiquitin-peptide extension in modified farnesylated form from said solution by transfer to and immobilization on a polymeric membrane selected from the group consisting of hydrocarbons, fluorocarbons, chlorofluorocarbons vinyl alcohols, and vinyl chlorides and copolymers and blends thereof and wherein the tritium in the immobilized farnesylated ubiquitin-peptide extension is detected.

11. The method of claim 10 wherein said polymeric membrane comprises a microporous polyvinylidenefluoride.

12. The method of claim 10 wherein said analyzing is accomplished by liquid scintillation spectroscopy.

13. The method of claim 6 wherein said enzyme being assayed for is carboxyl methyl transferase.

14. The method of claim 13 wherein said reaction mixture solution contains farnesyl-protein transferase and FPP, wherein said ubiquitin-peptide extension has the formula (SEQ ID NO:5):
Ub$_{73}$-Arg-Gly-Gly-Pro-Gly-Cys-Met-Ser-Cys-Lys-Cys-Val-Leu-Ser,
where Ub$_{73}$ stands for the N-terminal 73 amino acids from ubiquitin, is first farnesylated by FPP and wherein said one or more reagents needed to modify said peptide extension, in farnesylated form, when said carboxyl methyl transferase is present is AdeMet.

15. The method of claim 14 wherein said AdeMet is tritium labeled as [$^3$H-methyl]AdeMet.

16. The method of claim 15 wherein said analyzing of the reaction mixture is performed by terminating said incubation with an appropriate buffer, separating said farnesylated ubiquitin-peptide extension in modified form from said solution by electrophoresis followed by detection for the presence of tritium.

17. The method of claim 16 wherein said analyzing is accomplished by autoradiography.

18. The method of claim 2 wherein said enzyme being assayed for is a protein kinase.

19. The method of claim 18 wherein said peptide extension of ubiquitin-peptide extension contains the sequence (SEQ ID NO:1): Ser-Glu-Glu-Glu-Glu-Glu.

20. The method of claim 19 wherein said one or more reagents needed to modify said peptide extension when said protein kinase is present is a phosphorylating agent and which results in phosphorylation of said peptide extension.

21. The method of claim 20 wherein said phosphorylating agent is a member selected from the group consisting of ATP and GTP.

22. The method of claim 21 wherein said phosphorylating agent is $^{32}$P labeled.

23. The method of claim 22 wherein said ubiquitin-peptide extension is a member selected from the group consisting of
Ub$_{73}$-Arg-Gly-Gly-Met-Glu-Phe-Met-His-Ile-Ser-Pro-Pro-Glu-Pro-Glu-Ser-Glu-Glu-Glu-Glu-Glu-His-Ser-Ser (SEQ ID NO:2)

Ub$_{73}$-Arg-Gly-Gly-Met-Glu-Phe-Met-His-Glu-Ser-Glu-Glu-Glu-Glu-Glu-His-Ser-Ser (SEQ ID NO: 3) and Ub$_{73}$-Gln-Gly-Ala-Met-Glu-Ala-Ser-Glu-Glu-Glu-Glu-Glu-Phe (SEQ ID NO: 4)

where Ub$_{73}$ stands for the N-terminal 73 amino acids from ubiquitin.

24. The method of claim 23 wherein said analyzing of the reaction mixture is performed by terminating said incubation with an appropriate buffer, separating said ubiquitin-peptide extension in modified phosphorylated form from said solution followed by detection for the presence of $^{32}$PO$_4$ in the separated phosphorylated ubiquitin-peptide extension.

25. The method of claim 24 wherein said ubiquitin-peptide extension in modified phosphorylated form is first separated from endogenous protein substrates for other protein kinases present in the reaction mixture solution by heating the terminated reaction mixture under conditions effective for denaturing the endogenous protein substrates without significantly denaturing the ubiquitin-peptide extension and clarifying the heated reaction mixture to remove the endogenous substrates as denatured proteins leaving said phosphorylated ubiquitin-peptide extensions in solution.

26. The method of claim 24 wherein said separating is accomplished by binding said ubiquitin-peptide extension in modified phosphorylated form onto an ion-exchange paper and the $^{32}$PO$_4$ in the bound phosphorylated ubiquitin-peptide extension is detected by liquid scintillation spectroscopy.

27. The method of claim 24 wherein said separating is accomplished by acid precipitation of said ubiquitin-peptide extension in modified phosphorylated form and the $^{32}$PO$_4$ in the precipitated phosphorylated ubiquitin-peptide extension is detected by liquid scintillation spectrometry.

28. The method of claim 24 wherein said separating is accomplished by electrophoresis of said ubiquitin-peptide extension in modified phosphorylated form and the separated $^{32}$PO$_4$ is detected by autoradiography.

29. The method of claim 24 wherein the ubiquitin-peptide extension is:
Ub$_{73}$-Gln-Gly-Ala-Met-Glu-Ala-Ser-Glu-Glu-Glu-Glu-Glu-Phe (SEQ ID NO:4)

where Ub$_{73}$ represents the N-terminal 73 amino acids from ubiquitin.

30. The method of claim 24 wherein the ubiquitin-peptide extension is a member selected from the group consisting of
Ub$_{73}$-Arg-Gly-Gly-Met-Glu-Phe-Met-His-Ile-Ser-Pro-Pro-Glu-Pro-Glu-Ser-Glu-Glu-Glu-Glu-Glu-His-Ser-Ser (SEQ ID NO:2) and
Ub$_{73}$-Arg-Gly-Gly-Met-Glu-Phe-Met-His-Glu-Ser-Glu-Glu-Glu-Glu-Glu-His-Ser-Ser (SEQ ID NO:3)

where Ub$_{73}$ represents the N-terminal 73 amino acids from ubiquitin.

31. The method of claim 25 wherein the ubiquitin-peptide extension is a member selected from the group consisting of
Ub$_{73}$-Arg-Gly-Gly-Met-Glu-Phe-Met-His-Ile-Ser-Pro-Pro-Glu-Pro-Glu-Ser-Glu-Glu-Glu-Glu-Glu-His-Ser-Ser (SEQ ID NO:2) and
Ub$_{73}$-Arg-Gly-Gly-Met-Glu-Phe-Met-His-Glu-Ser-Glu-Glu-Glu-Glu-Glu-His-Ser-Ser (SEQ ID NO:3)

where Ub$_{73}$ represents the N-terminal 73 amino acids from ubiquitin.

32. The method of claim 31 wherein said phosphorylated ubiquitin-peptide extension remaining in solution after heat denaturation and separation of endogenous substrates are incubated with a ubiquitin carboxyl-terminal hydrolase thereby cleaving the phosphorylated peptide extension from ubiquitin, separating said phosphorylated peptide extension from said solution by electrophoresis followed by sequencing the phosphorylated peptide extension to determine the phosphorylated residues.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 6 amino acid residues
        ( B ) TYPE: amino acid
        ( D ) TOPOLOGY: linear     ( x i ) SEQUENCE DESCRIPTION: SEQ ID NO:1:

Ser Glu Glu Glu Glu Glu
            5

( 2 ) INFORMATION FOR SEQ ID NO:2:

( i ) SEQUENCE CHARACTERISTICS:
        ( A ) LENGTH: 24 amino acid residues
        ( B ) TYPE: amino acid
        ( D ) TOPOLOGY: linear     ( x i ) SEQUENCE DESCRIPTION: SEQ ID NO:2:

Arg Gly Gly Met Glu Phe Met His Ile Ser Pro Pro Glu Pro Glu Ser Glu
            5                        10                 15

Glu Glu Glu Glu His Ser Ser
       20

( 2 ) INFORMATION FOR SEQ ID NO:3:

( i ) SEQUENCE CHARACTERISTICS:
        ( A ) LENGTH: 18 amino acid residues
        ( B ) TYPE: amino acid
        ( D ) TOPOLOGY: linear     ( x i ) SEQUENCE DESCRIPTION: SEQ ID NO:3:

Arg Gly Gly Met Glu Phe Met His Glu Ser Glu Glu Glu Glu His Ser Ser
            5                        10                 15

Ser ( 2 ) INFORMATION FOR SEQ ID NO:4:

( i ) SEQUENCE CHARACTERISTICS:
        ( A ) LENGTH: 13 amino acid residues
        ( B ) TYPE: amino acid
        ( D ) TOPOLOGY: linear     ( x i ) SEQUENCE DESCRIPTION: SEQ ID NO:4:

Gln Gly Ala Met Glu Ala Ser Glu Glu Glu Glu Glu Phe
            5                        10

( 2 ) INFORMATION FOR SEQ ID NO:5:

( i ) SEQUENCE CHARACTERISTICS:
        ( A ) LENGTH: 14 amino acid residues
        ( B ) TYPE: amino acid
        ( D ) TOPOLOGY:linear     ( x i ) SEQUENCE DESCRIPTION: SEQ ID NO:5:

Arg Gly Gly Pro Gly Cys Met Ser Cys Lys Cys Val Leu Ser
            5                        10

( 2 ) INFORMATION FOR SEQ ID NO:6:

( i ) SEQUENCE CHARACTERISTICS:
        ( A ) LENGTH: 13 amino acid residues
        ( B ) TYPE: amino acid
        ( C ) TOPOLOGY: linear     ( x i ) SEQUENCE DESCRIPTION: SEQ ID NO:6:

Arg Gly Gly Met Glu Phe Met His Glu Ser His Ser Ser (2) INFORMATION FOR SEQ ID NO:7:

(i) SEQUENCE CHARACTERISTICS:
        (A) LENGTH: 19 amino acid residues
        (B) TYPE: amino acid
        (D) TOPOLOGY: linear     (xi) SEQUENCE DESCRIPTION: SEQ ID NO:7:

Arg Gly Gly Met Glu Phe Met His Ile Ser Pro Pro Glu Pro Glu Ser
                5                      10                  15

His Ser Ser (2) INFORMATION FOR SEQ ID NO:8:

(i) SEQUENCE CHARACTERISTICS:
        (A) LENGTH: 10 amino acid residues
        (B) TYPE: amino acid
        (D) TOPOLOGY: linear     (xi) SEQUENCE DESCRIPTION: SEQ ID NO:8:

Met Glu Ala Ser Glu Glu Glu Glu Glu Phe
            5                    10

(2) INFORMATION FOR SEQ ID NO:9:

(i) SEQUENCE CHARACTERISTICS:
        (A) LENGTH: 14 amino acid residues
        (B) TYPE: amino acid
        (D) TOPOLOGY: linear     (xi) SEQUENCE DESCRIPTION: SEQ ID NO:9:

Arg Gly Gly Pro Gly Cys Met Ser Cys Lys Ser Val Leu Ser
              5                    10

(2) INFORMATION FOR SEQ ID NO:10:

(i) SEQUENCE CHARACTERISTICS:
        (A) LENGTH: 63 nucleic acid residues
        (B) TYPE: nucleic acid
        (C) STRANDEDNESS: single
        (D) TOPOLOGY: linear     (xi) SEQUENCE DESCRIPTION: SEQ ID NO:10:

AGACTAAGAG GTGGTCCCGG ATGCATGTCT TGTAAATGTG TACTATCATG AGGTACCGAG  60

CTC  63

(2) INFORMATION FOR SEQ ID NO:11:

(i) SEQUENCE CHARACTERISTICS:
        (A) LENGTH: 11 amino acid residues
        (B) TYPE: amino acid
        (D) TOPOLOGY: linear     (xi) SEQUENCE DESCRIPTION: SEQ ID NO:11:

Pro Gly Cys Met Ser Cys Lys Cys Val Leu Ser
            5                    10

(2) INFORMATION FOR SEQ ID NO:12:

(i) SEQUENCE CHARACTERISTICS:
        (A) LENGTH: 22 nucleic acid residues
        (B) TYPE: nucleic acid
        (C) STRANDEDNESS: single
        (D) TOPOLOGY: linear     (xi) SEQUENCE DESCRIPTION: SEQ ID NO:12:

TCTTGTAAAT CAGTACTATC AT 22

( 2 ) INFORMATION FOR SEQ ID NO:13:

( i ) SEQUENCE CHARACTERISTICS:
        ( A ) LENGTH: 11 amino acid residues
        ( B ) TYPE: amino acid
        ( D ) TOPOLOGY: linear     ( x i ) SEQUENCE DESCRIPTION: SEQ ID NO:13:

Pro Gly Cys Met Ser Cys Lys Ser Val Leu Ser
              5                 10